US 6,307,476 B1

(12) United States Patent
Smith et al.

(10) Patent No.: US 6,307,476 B1
(45) Date of Patent: Oct. 23, 2001

(54) SMART BINARY SWITCH FOR USE WITH AN ELECTRONIC PATIENT MONITOR

(75) Inventors: Toby E. Smith, Broken Arrow; Patrick W. Lovely, Tulsa, both of OK (US)

(73) Assignee: Bed-Check Corporation, Tulsa, OK (US)

( * ) Notice: Subject to any disclaimer, the term of this patent is extended or adjusted under 35 U.S.C. 154(b) by 0 days.

(21) Appl. No.: 09/285,956

(22) Filed: Apr. 2, 1999

(51) Int. Cl.[7] .................................................. G08B 23/00
(52) U.S. Cl. ...................... 340/573.1; 340/644; 340/650; 340/651; 340/652
(58) Field of Search ................................ 340/573.1, 644, 340/650, 651, 652

(56) References Cited

U.S. PATENT DOCUMENTS

| 4,179,692 |   | 12/1979 | Vance ................................... 340/573 |
| 4,295,133 |   | 10/1981 | Vance ................................... 340/573 |
| 4,484,043 |   | 11/1984 | Musick et al. ...................... 200/85 R |
| 4,565,910 |   | 1/1986  | Musick et al. ...................... 200/85 R |
| 4,633,237 | * | 12/1986 | Tucknott et al. ..................... 340/573 |
| 4,700,180 |   | 10/1987 | Vance ................................... 340/573 |
| 4,907,845 | * | 3/1990  | Wood ................................... 340/573 |
| 5,144,284 | * | 9/1992  | Hammett ............................. 340/573 |
| 5,184,112 | * | 2/1993  | Gusakov .............................. 340/573 |
| 5,235,319 | * | 8/1993  | Hill et al. ............................. 340/573 |
| 5,276,432 | * | 1/1994  | Travis ................................... 340/573 |
| 5,293,979 | * | 3/1994  | Levasseur ............................. 194/317 |
| 5,410,297 | * | 4/1995  | Joseph et al. ........................ 340/573 |
| 5,554,835 |   | 9/1996  | Newham .............................. 200/85 R |
| 5,602,428 | * | 2/1997  | Schultz et al. ....................... 307/119 |
| 5,623,760 |   | 4/1997  | Newham ................................ 29/622 |
| 5,633,627 |   | 5/1997  | Newham .............................. 340/573 |
| 5,640,145 |   | 6/1997  | Newham .............................. 340/573 |
| 5,751,214 | * | 5/1998  | Cowley et al. ...................... 340/573 |
| 5,780,798 | * | 7/1998  | Hall-Jackson ...................... 200/85 R |
| 5,808,552 | * | 9/1998  | Wiley et al. ......................... 340/573 |
| 5,844,488 | * | 12/1998 | Musick ................................ 340/573 |

* cited by examiner

*Primary Examiner*—Jeffery Hofsass
*Assistant Examiner*—Tai T. Nguyen
(74) *Attorney, Agent, or Firm*—Fellers, Snider, Blankenship, Bailey & Tippens, P.C.

(57) ABSTRACT

This invention relates generally to monitoring systems and more particularly concerns devices and systems used to monitor bed patients in hospital or other care-giving environments. In accordance with a first aspect of the instant invention, there is provided a binary switch-type device (e.g., a "mat") for use in patient monitoring situations which contains, in addition to a conventional patient detection circuit, identification circuitry that can be sensed by an attached electronic monitor. The identification circuitry can be sensed by the electronic monitor and is designed to be configured to serve many different purposes, including, by way of example only, identification of the type of mat attached thereto, detection of connectivity problems, tracking mat usage time, and identifying mats that are nearing the end of their useful lives.

6 Claims, 3 Drawing Sheets

SMART BINARY SWITCH FOR USE WITH AN ELECTRONIC PATIENT MONITOR

FIELD OF THE INVENTION

This invention relates generally to monitoring systems and more particularly concerns devices and systems used to monitor seated or lying patients in homes or in medical environments such as hospitals, institutions, and other caregiving environments.

BACKGROUND OF THE INVENTION

It is well documented that certain individuals, including elderly and post-surgical patients, are at a heightened risk of falling. There are many reasons for this but, broadly speaking, these individuals are often afflicted by gait and balance disorders, weakness, dizziness, confusion, visual impairment, and postural hypotension (i.e., a sudden drop in blood pressure that causes dizziness and fainting), all of which are recognized as potential contributors to a fall. Additionally, cognitive and functional impairment, and sedating and psychoactive medications are also well recognized risk factors.

A fall places the patient at risk of various injuries including sprains, fractures, and broken bones—injuries which in some cases can be severe enough to eventually lead to a fatality. Of course, those most susceptible to falls are often those in the poorest general health and least likely to recover quickly from their injuries. In addition to the obvious physiological consequences of fall-related injuries, there are also a variety of adverse economic and legal consequences that include the actual cost of treating the victim and, in some cases, caretaker liability issues.

In the past, it has been commonplace to treat patients that are prone to falling by limiting their mobility through the use of restraints, the underlying theory being that if the patient is not free to move about, he or she will not be as likely to fall. However, research has shown that restraint-based patient treatment strategies are often more harmful than beneficial and should generally be avoided—the emphasis today being on the promotion of mobility rather than immobility. Among the more successful mobility-based strategies for fall prevention include interventions to improve patient strength and functional status, reduction of environmental hazards, and staff identification and monitoring of high-risk hospital patients and nursing home residents.

Of course, monitoring high-risk patients, as effective as that care strategy might appear to be in theory, suffers from the obvious practical disadvantage of requiring additional staff if the monitoring is to be in the form of direct observation. Thus, the trend in patient monitoring has been toward the use of electrical devices to signal changes in a patient's circumstance to a care-giver who might be located either nearby or remotely at a central monitoring facility, such as a nurse's station. The obvious advantage of an electronic monitoring arrangement is that it frees the caregiver to pursue other tasks away from the patient. Additionally, when the monitoring is done at a central facility a single nurse can monitor multiple patients which can result in decreased staffing requirements.

Generally speaking, electronic monitors work by first sensing an initial status of a patient, and then generating a signal when that status changes, e.g., he or she has sat up in bed, left the bed, risen from a chair or toilet seat, etc., any of which situations could pose a potential cause for concern in the case of an at-risk patient. Electronic bed and chair monitors typically use a pressure sensitive switch in combination with a separate monitor/microprocessor. In a common arrangement, a patient's weight resting on a pressure sensitive mat (i.e., a "sensing" mat) completes an electrical circuit, thereby signaling the presence of the patient to the microprocessor. When the weight is removed from the pressure sensitive switch, the electrical circuit is interrupted, which fact is sensed by the microprocessor. The logic that drives the monitor is typically programmed to respond to the now-opened circuit by triggering some sort of alarm—either electronically (e.g., to the nursing station via a conventional nurse call system) or audibly (via a built-in siren). Some examples of monitoring devices that operate in this general fashion may be found in U.S. Pat. Nos. 4,179,692, 4,295,133, 4,700,180, 5,633,627, and 5,640,145, the disclosures of which are incorporated herein by reference. Additionally, many variations of this arrangement are possible and electronic monitoring devices that track changes in other patient variables (e.g., wetness/enuresis, patient activity, etc.) are available for some applications.

However, present mats and other sensing devices for use in patient monitoring suffer from a number of disadvantages. For example, a problem with present mats and monitoring systems is that they do not provide a means for the monitor to identify the particular type of mat attached thereto. A monitor manufacturer might wish to do this for any number of reasons. For example, providers of medical equipment can be held liable for damages caused to a patient because of a failure in their monitoring system, a fact that argues for a method of making certain that mat attached thereto is fully compatible with the monitor.

Additionally, a monitor manufacturer would like to have some assurance that the mats that are attached to his or her unit meet basic standards of quality, as the monitor could blamed—at least initially—for a failure in a mat that allows a patient to leave the bed unnoticed. Further, for quality control purposes, it might be desired in some applications to be able to track the length of time that a particular mat has been in place, thereby assisting the health care provider in identifying mats that might be nearing the end of their useful lives.

Still further, it would be useful in some circumstances to be able to automatically identify whether the switch that is connected to the monitor is of the proper type for this application. For example, pressure-sensitive chair monitors should not be used to sense wetness in beds and vise versa. Where the possibility exists that the mats designed for different applications might be interchanged, it would be of benefit to the manufacturer of the mats and/or electronic monitors to be able to recognize that fact and notify the caregiver accordingly.

Finally, it is a problem with present mats and monitoring systems that they do not provide any means of automatically determining whether or not the electrical connection between the monitor and mat is sound. It is well known to those skilled in the art that the wiring that interconnects the mat and monitor is exposed to various stresses that can result in impaired functionality or even equipment failure. For example, if the interconnecting wire is not making continuous contact at one end or the other, the monitor will see an "open" circuit, whether or not the patient is actually present in the bed. To test the interconnection, it is necessary to put weight on the mat, which would usually be done by placing the patient upon it, thereby closing the detection circuit which event can then be sensed by the monitor. Where there is problem in the connection, the patient will have to be roused out of bed so that the mat can be changed. This disturbs the patient and takes additional caregiver time. It would be a tremendous advantage in some situations to be able to have the electronic monitor quickly and automatically indicate to the caregiver when there is there is no electrical continuity between the mat and the monitor.

Heretofore, as is well known in the bed monitor arts, there has been a need for an invention to address and solve the above-described problems. Accordingly, it should now be recognized, as was recognized by the present inventors, that there exists, and has existed for some time, a very real need for a smart mat and monitoring system that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

In accordance with a first aspect of the instant invention, there is provided a binary switch-type device (e.g., a "mat") for use in patient monitoring situations which contains, in addition to a conventional patient detection circuit, identification circuitry that can be read by an attached electronic monitor in order to determine the type of mat that is attached thereto (i.e., a "smart" mat). Additionally, and by way of example only, the identification circuitry also provides a means for the electronic monitor to recognize certain types of electrical interconnection failures, to identify mats that are nearing the end of their useful lives, to warn the caregiver when a mat that is designed for one operating environment/application is used in another, etc.

In the preferred embodiment, unused electrical wires in the connecting line between the binary switch and monitor are used to allow access by a microprocessor within the electronic monitor to an integrity/identification/verification/validation circuit which is preferably made a part of the mat. This circuit might take many forms including simple resistor or capacitor circuits, or more complex circuits that might involve use of an integrated circuit. In any case the ultimate goal is the same: identification and/or recognition by the monitor of the mat that has been attached thereto. This identification might take place at any time, but preferably will take place at least when the unit is powered up or reset. It might also be performed at scheduled time intervals or random times, depending the needs of the particular application.

The foregoing has outlined in broad terms the more important features of the invention disclosed herein so that the detailed description that follows may be more clearly understood, and so that the contribution of the instant inventor to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Further, the disclosure that follows is intended to cover all alternatives, modifications and equivalents as may be included within the spirit and scope of the invention as defined by the appended claims. Finally, it should be understood that the phraseology and terminology employed herein are for the purpose of description and should not be regarded as limiting, unless the specification specifically so limits the invention.

While the instant invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

BRIEF DESCRIPTION OF THE DRAWINGS

Other objects and advantages of the invention will become apparent upon reading the following detailed description and upon reference to the drawings in which:

FIG. 2 contains a schematic diagram of two preferred embodiments of the instant invention.

DETAILED DESCRIPTION OF THE INVENTION

General Background

According to a preferred aspect of the instant invention, there is provided a patient sensor for use with an electronic bed patient monitor, wherein the sensor incorporates additional circuitry which is accessible by the electronic monitor and that can be read thereby. In more particular, two preferred uses of the sensor circuitry include the identification by the monitor of the type of mat connected thereto and the diagnosis of some connectivity-type problems.

Figure 1:
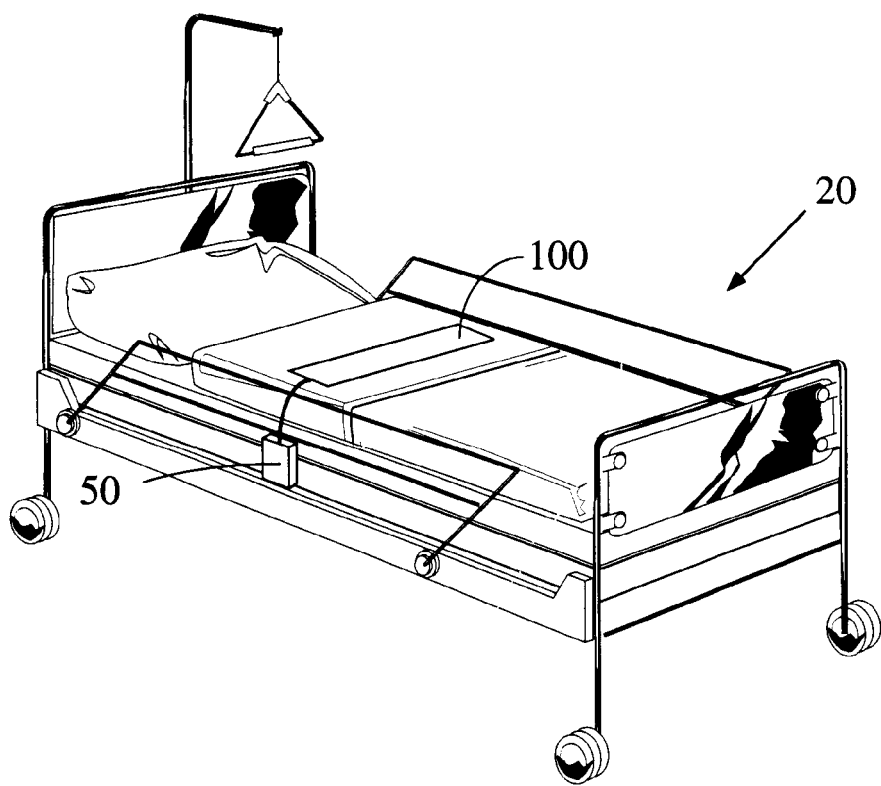
FIG. 1 illustrates the general environment of the instant invention.

Turning first to FIG. 1 wherein the general environment of the instant invention is illustrated, in a typical arrangement a sensing mat 100 is placed on a hospital bed 20 where it will lie beneath a weight-bearing portion of the reclining patient's body, usually the buttocks and/or shoulders. Generally speaking, the mat 100/monitor 50 combination works as follows. When a patient is placed atop the mat 100, the patient's weight compresses the mat 100 and closes an electrical circuit 215, which closure is sensed by the attached electronic patient monitor 50. When the patient attempts to leave the bed, weight is removed from the sensing mat 100, thereby breaking the electrical circuit 215, which interruption is sensed by the attached electronic patient monitor 50. The patient monitor then signals the caregiver per its pre-programmed instructions. Note that additional electronic connections not pictured in this figure might include a monitor 50 to nurse call station connection, a monitor 50 to computer connection, and a monitor power cord—although the monitor 50 can certainly be configured to be battery operated.

Preferred Hardware Arrangement

Figure 2A:
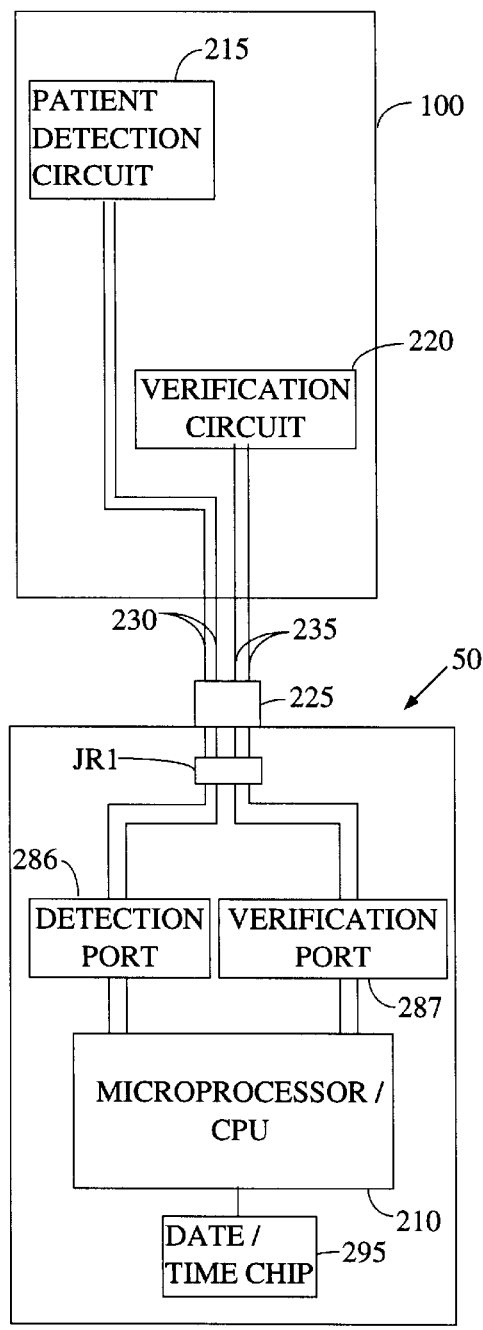
FIG. 2A illustrates a mat which incorporates the validation circuit internally and FIG. 2B illustrates a mat in which the validation circuit is external.

A first preferred embodiment of the instant mat 100 and an associated electronic patient monitor 50 are illustrated in FIG. 2A. In that figure, the patient monitor 50 is shown as including a microprocessor 210, which microprocessor controls the sensing and response of the monitor 50 to changes in the patient detection circuit 215. As was explained previously, the patient detection circuit 215 preferably consists of an electronic circuit that changes states when a patient's weight is placed upon the mat 100, e.g. it might change from an "open" circuit to a "closed" circuit or vice versa. More generally, this circuit might be continuously responsive to any other environmental condition such as patient activity, wetness, etc. However, the heart of the instant invention is the validation circuit 220, which is preferably made to be a part of the sensing mat 100 as indicated in FIG. 2A.

As is illustrated in FIG. 2A, in the preferred embodiment the mat 100 and monitor 50 are interconnected by a single RJ-11 type electrical connector 225 through which pass four electrical lines: one pair 230 in electrical communication with the patient detection circuit 215 and the other pair 235 in electrical communication with the validation circuit 220. Note that this is just a preferred embodiment and that other arrangements might include more than four electrical lines (or fewer) and it is well within the ability of one skilled in the art to devise such alternative arrangements. Additionally, connector 225 could be separated into two separate connectors without changing the spirit of the instant invention and it would be well within the ability of one skilled in the art to modify the monitor 50 accordingly.

Microprocessor 210 reads electrical lines 230 through detection port 286 and responds to changes in that circuit according to its pre-assigned instructions. Typically, the microprocessor 210 will be programmed to initiate some sort of alarm if a change (e.g., a discontinuity) is detected in the patient detection circuit 215, which change would most likely indicate that the patient has left the bed 20. The alarm triggered by the monitor 50 might be either a local alarm (e.g., generated within the monitor 50 itself) or a remote alarm in the hall or at a nurses station. This portion of the mat 100/monitor 50 combination is of a conventional design.

The particular patient monitor circuit 215 which used within the mat 100 is immaterial to the operation of this invention, although it must generally be in the form of a binary switch, a binary switch or sensor being one that is capable of sensing at least two conditions and responding to same via distinct electronic signals. Although a pressure sensitive switch is the binary switch of choice for use in the preferred embodiment, other types of switches could work as well. Examples of binary switches/mats which would be suitable for use with the instant invention include those found in U.S. Pat. Nos. 5,623,760, 5,554,835, 4,484,043, 4,545,910, and in co-pending patent application Ser. No. 09/096,404, filed Jun. 11, 1998, for a toilet seat monitor, the disclosures of which are specifically incorporated herein by reference. So, for purposes of this disclosure, the term "mat" will be taken to mean conventional bed and chair mats, as well as other sorts of sensors which detect patient conditions and are useful in patient monitoring.

However, of most interest for purposes of the instant invention is the validation circuit 220 and its many applications in patient monitoring. Turning again to FIG. 2A, in this figure the basic electronic interconnections for a mat 100 that has been equipped with the validation circuit 220 of the instant invention have been illustrated. Two unused lines 235 that are normally available within an RJ-11-type connector 225 are preferably used to establish an electrical connection between the monitor CPU 210 and the validation circuit 220. The monitor 50 senses the state of validation circuit 220 by way of validation port 287. Additionally, provision has been made in the preferred embodiment for inclusion of a date/time chip 295 which can be read by the CPU 210 and used to "date stamp" various events that are sensed thereby. Details of one possible hardware arrangement that would accommodate this sort of operation may be found in the patent application Ser. No. 09/257,750 "Microprocessor Based Bed Patient Monitor", filed Feb. 25, 1999, which is a continuation of application Ser. No. 09/031,363 filed Feb. 26, 1998, the disclosures of which are incorporated herein by reference.

Note that, although the preferred embodiment of the instant invention is designed to be used with an electronic patient monitor containing a microprocessor, that is not an essential element of the instant invention and it is certainly possible and within the ability of one of ordinary skill in the art to construct a simple analog patient monitor that is responsive to the patient detection circuit and identification circuits, but which contains no computer components. Thus, when the term "electronic patient monitor" is used herein, that term should be interpreted in its broadest sense to include both patient monitors that have—and those that do not have—controlling microprocessors.

The precise hardware that would be included within the monitor 50 to query the validation circuit 220 will be a function of the sort of electrical circuit that has been installed there. In the simplest situation, the circuit could consist of a simple closed electrical loop. The monitor 50 could use this loop to perform a continuity check between the monitor 50 and the mat 100. Then, if no electrical current can be detected through the circuit, it is likely that the mat 100/monitor 50 connection has been damaged in some way, or that the mat 50 is not properly plugged into the monitor. Either way, the caregiver should be immediately notified so that corrective action may be taken before the patient is placed on the mat 100. Note that this continuity test—and the other tests described below—may be performed independently of whether a patient is actually present on the mat. This is a significant advance over the existing state-of-the-art in patient monitors.

By way of a next simple example of a circuit that would be appropriate for use with the instant invention, validation circuit 220 might consist of a precision resistor of, say, 100 ohms that is placed across the leads 235. The monitor CPU 210 would then cause a known current to be applied to the leads 235 on the monitor end and, thereafter, measure the resulting voltage (which is related to the resistance in the validation circuit 220 via a well known equation). Then, if the resistance of the circuit as measured at the monitor is not within, say, 1% of 100 ohms, the CPU 210 will sound an alarm to notify the caregiver that there is some problem with the mat. Obviously, if the measured resistance is too high, that would indicate a break in the electrical connection between the monitor 50 and validation circuit 220. Resistances that deviate from the expected resistance might indicate physical damage to the circuit or poor connectivity between mat 100 and monitor 50.

In an alternative embodiment, the resister might be chosen in such as way as to communicate some information to the monitor. For example, a 30 ohm resister might be used with mats having a 30-day useful life, and a 100 ohm resister with a 100 day mat, etc. Obviously, this sort of arrangement would make it possible for an appropriately designed monitor 50 to track the usage time of a mat that has been continuously connected thereto and signal when the mat 100 nears the end of its recommend period of use.

Alternatively, the validation circuit 220 might instead be formed from a capacitor, an inductor, or some combination of one or more of each component. In this case, the CPU 210 can sense the presence of the validation circuit 220 by testing the reactance of the circuit formed thereby. As was described previously, if the measured reactance of the circuit does not match a predetermined value—which might indicate a poor electrical connection or that a mat of the improper type has been connected to the monitor 50—an alarm would be sounded.

As a final example of the sort of circuit that would be appropriate for use with the instant invention, the inventors contemplate that it could prove to be useful in some applications to install a ROM chip, or even a flash RAM chip, within the mat 100. The ROM chip could contain and dispense a wide variety of information including, by way of example, a mat serial number, a mat manufacture date/lot number, and various other parameters that would define the sorts of uses to which this mat might be put. Flash RAM, on the other hand, could contain all of the foregoing and, additionally, values that might be modified by the monitor 50. One obvious example of the sort of information that might be placed in flash RAM would be a running total of the amount of time that the mat 100 has been in service. Communications between the monitor 50 and the chip would preferably be handled via the $I^2C$ communications protocol which has become the predominant standard for low cost inter-chip communications (i.e., "Inter-IC", which is a standard means of providing a two-wire communication link between integrated circuits). Detailed information on the chip and the $I^2C$ protocol may be found in the Microchip Nonvolatile Memory Products databook.

Figure 2B:
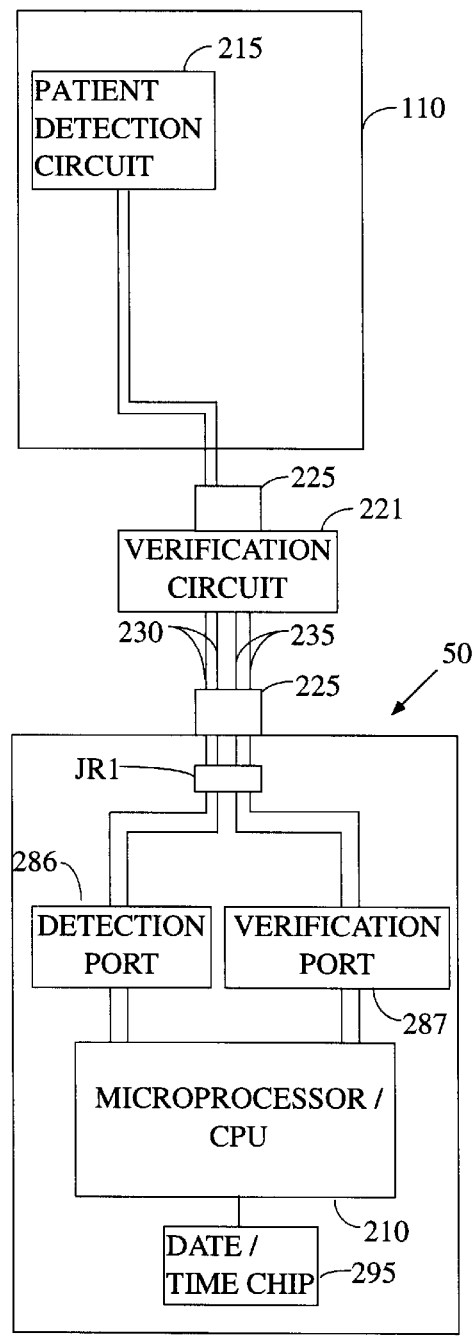

As illustrated in FIG. 2A, the validation circuit 220 is preferably made a part of—and included within—the mat 100 (e.g., FIG. 2A). However, it is anticipated by the instant inventors that the validation circuit 220 could be incorporated within the RJ-11-type connector 225 for some applications or even designed to be a separate module which is positioned between the mat 100 and the monitor 50 (e.g., FIG. 2B, part 221). In any case, the physical location of the validation circuit is immaterial to the instant application, except that its functionality may vary somewhat depending upon where it is positioned with respect to the mat 100.

General Method of Operation

Figure 3:
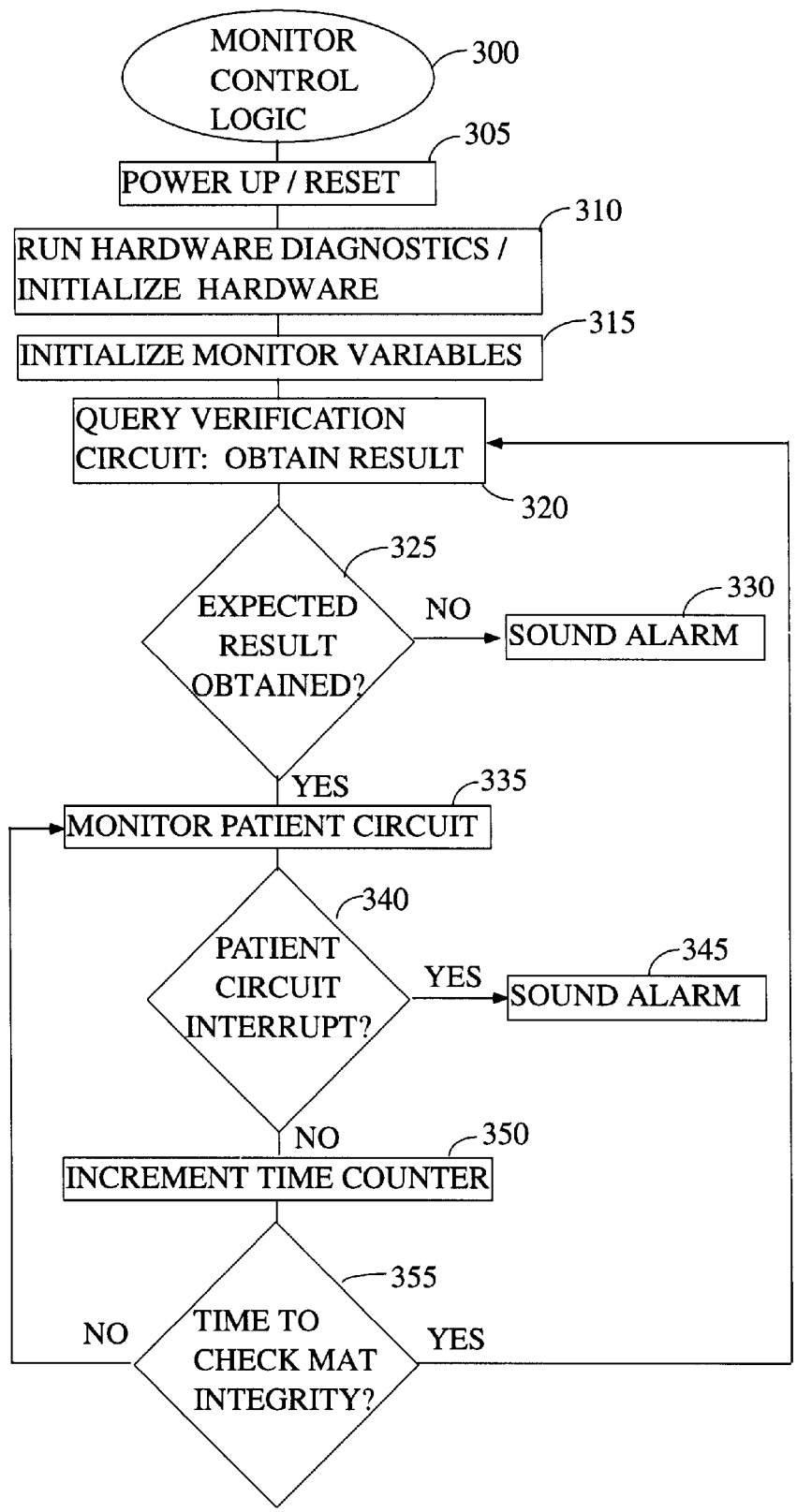
FIG. 3 contains a flow chart that illustrates some of the principal steps in the preferred electronic monitor control logic.

In normal operation—and if the mat 100 is used with a patient monitor 50 having a microprocessor—the principle steps in the monitor's logic flow are generally as indicated in FIG. 3. Note that, depending on the exact model of electronic monitor, there will be a variety of switches on its exterior that allow the attendant to arm or disarm the device, temporarily suspend its operation, change its response parameters or hold and delay times, etc. Although these sorts of activities are not considered within FIG. 3, those skilled in the art will understand how the figure could easily be modified to illustrate them.

After the monitor 50 is first powered-up 305 (or reset) it will typically perform some basic hardware diagnostics and initialize local program variables (steps 310 and 315). Next, the monitor 50 will preferably perform an initial query of the validation circuit (320) using methods such as those suggested previously. In its broadest sense, this query may be thought of as a "signal" that is transmitted to the validation circuit 320. The signal might be as simple as the application of a specific voltage across the electrical lines 235, or it could be the more complicated signaling scheme required by the $I^2C$ protocol.

Needless to say, the precise type of "query" employed by the monitor 50 will depend on—and need to be matched to—the general nature of the validation circuit 220. From the initial query, the CPU 210 will obtain a test result (320) of some sort. By comparing (step 325) the results of the query 320 with expected outcomes that have been supplied by, for example, the manufacturer, the monitor will be able to identify certain kinds of electrical problems and distinguish some sorts mats from others. For those instances when the result of the query is not as expected, an alarm will preferably be sounded 330. The alarm might be limited to the loudspeaker of the local monitor 50 or transmitted further to the nurses station.

Assuming that the initial check of the mat 50 yields a favorable result, the monitor 100 will then normally begin tracking the condition of the patient detection circuit 215 in the mat (steps 335 and 340) and will generate a response when the patient circuit 215 is interrupted (steps 340 and 345). As part of the on-going tracking effort, additional/intermittent testing of the validation circuit 320 could be performed (steps 350 and 320) at time intervals specified by the user (steps 350 and 355). Although the validation circuit 220 could be continuously monitored, that would normally not be required and, in the preferred embodiment, the mat integrity/validation would be redetermined at intervals of, say, five minutes.

Of course, sounding an alarm might not be the end of the matter. In some cases, the monitor 50 might be programmed to briefly sound an alarm to simply warn the caregiver that, for example, a mat 100 is nearing the end of its useful life and should be replaced. The alarm would automatically cease after a relatively short period of time for these sorts of warnings. In other cases, a simple "acknowledgement" switch could be provided that would turn off the alarm and let the caregiver continue as before using the same equipment. On the other hand, when the problem is more serious (e.g., when mat 100 has been placed into an environment for which it was not designed) that situation might require the caregiver to manually override the alarm, an operation that would preferably be logged within the monitor 50 and/or transmitted to the central monitoring station. Finally, in some extreme circumstances the monitor 50 might disable itself and sound a continuous alarm until the connected mat 100 is removed. Circumstances where that might be necessary include instances where the monitor has detected a lack of electrical continuity between the monitor 50 and the mat 100. Clearly, many variations of this arrangement are possible and have been contemplated by the instant inventors.

CONCLUSIONS

Although the preceding text has occasionally referred to the electronic monitor of the instant invention as a "bed" monitor and the sensing switch a "mat", that was for purposes of specificity only and not out of any intention to limit the instant invention to that one application. In fact, the potential range of uses of this invention is much broader than bed-monitoring alone and might include, for example, use with a chair monitor, a toilet monitor, or other patient monitor applications, each of which is configurable as a binary switch, a binary switch being one that is capable of sensing at least two conditions and responding to same via distinct electronic signals. In the preferred embodiment, those two conditions would be the presence of patient and the absence of a patient from a monitored area. Although a pressure sensitive switch is the binary switch of choice for use in the preferred embodiment, other types of switches could work as well for some applications including, for example, sensors that detect moisture. Additionally, it should be noted that the use of the term "binary" is not intended to limit the instant invention to use only with sensors that can send only two signal types. Instead, binary switch will be used herein in its broadest sense to refer to any sort sensor that can be utilized to sense the condition or location of a patient, even if that sensor can generate a multitude of different signals.

Thus, it is apparent that there has been provided, in accordance with the invention, a patient sensor and method of operation of the sensor that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. A device for detecting a presence or an absence of a patient, comprising:
   (a) a binary switch, said binary switch being responsive to at least two conditions,
      (a1) a first condition corresponding to said presence of said patient on said binary switch, and,
      (a2) a second condition corresponding to said absence of said patient from said binary switch;
   (b) a validation circuit;
   (c) a first electrical connection, said first electrical connection being in electrical communication with said binary switch;
   (d) a second electrical connection, said second electrical connection being in electrical communication with said validation circuit; and,
   (e) an electronic patient monitor in electrical communication with said first electrical connection and said second electrical connection, wherein,
      (e1) said electronic patient monitor is responsive to at least said binary switch and said validation circuit, and,
      (e2) said electronic patient monitor has a microprocessor in electrical communication with at least said second electrical connection, said microprocessor at least for reading said validation circuit and being responsive thereto.

2. A device according to claim 1, wherein said microprocessor is in electrical communication with said first electrical connection and said second electrical connection, said microprocessor
   detecting at least said first and second condition of said binary switch and being responsive thereto, and,
   reading said validation circuit and being responsive thereto.

3. A method by which an electronic patient monitor may identify a patient sensor attached thereto, wherein is provided the apparatus of claim 1, said microprocessor programmed to perform the steps of:
   (a) causing a signal to be generated;
   (b) transmitting said signal to said validation circuit;
   (c) sensing a response to said signal from said validation circuit;
   (d) comparing said sensed response with at least one predetermined response; and,
   (e) causing said electronic monitor to indicate an alarm condition if said sensed response does not at least approximately correspond to at least one of said at least one predetermined responses.

4. A method identifying a patient sensor, wherein is provided an electronic patient monitor in electrical communication with a binary switch, said binary switch having a validation circuit associated therewith, comprising the steps of:
   (a) causing a signal to be generated within said electronic patient monitor;
   (b) transmitting said signal to said validation circuit;
   (c) sensing a response to said signal from said validation circuit;
   (d) comparing said sensed response with at least one predetermined response; and,
   (e) causing said electronic monitor to indicate an alarm condition if said sensed response does not at least approximately correspond to at least one of said at least one predetermined responses.

5. A method according to claim 4, wherein said signal is a constant voltage signal.

6. A method according to claim 4, wherein said signal conforms to an $I^2C$ protocol.

* * * * *